(12) United States Patent
Saito et al.

(10) Patent No.: US 11,865,560 B2
(45) Date of Patent: Jan. 9, 2024

(54) LIQUID EJECTION DEVICE

(71) Applicant: Seiko Epson Corporation, Tokyo (JP)

(72) Inventors: Yuji Saito, Shiojiri (JP); Hirokazu Sekino, Chino (JP); Takeshi Seto, Shiojiri (JP); Hideki Kojima, Matsumoto (JP); Takahiro Matsuzaki, Shiojiri (JP)

(73) Assignee: SEIKO EPSON CORPORATION

( * ) Notice: Subject to any disclaimer, the term of this patent is extended or adjusted under 35 U.S.C. 154(b) by 194 days.

(21) Appl. No.: 16/943,009

(22) Filed: Jul. 30, 2020

(65) Prior Publication Data

US 2021/0031223 A1 Feb. 4, 2021

(30) Foreign Application Priority Data

Jul. 31, 2019 (JP) ................... 2019-140788

(51) Int. Cl.
*B05B 12/08* (2006.01)
*B05B 17/06* (2006.01)

(52) U.S. Cl.
CPC .......... *B05B 12/082* (2013.01); *B05B 12/085* (2013.01); *B05B 17/06* (2013.01)

(58) Field of Classification Search
CPC ...... B05B 12/082; B05B 12/085; B05B 17/06
See application file for complete search history.

(56) References Cited

U.S. PATENT DOCUMENTS

| 8,511,251 | B2* | 8/2013 | Sato | C23C 24/04 |
| | | | | 118/308 |
| 9,950,334 | B1* | 4/2018 | Massey | B05B 12/22 |
| 2007/0200898 | A1* | 8/2007 | Ueno | B41J 2/1433 |
| | | | | 347/55 |
| 2010/0116900 | A1* | 5/2010 | Wurz | B05B 7/045 |
| | | | | 239/8 |
| 2011/0303762 | A1* | 12/2011 | Wegelin | F04B 17/003 |
| | | | | 222/190 |
| 2014/0367485 | A1* | 12/2014 | Kojima | B05B 14/30 |
| | | | | 239/102.1 |
| 2018/0244040 | A1 | 8/2018 | Jeute et al. | |

FOREIGN PATENT DOCUMENTS

| CN | 107257738 A | | 10/2017 | |
| JP | H0690957 A | * | 4/1994 | ............ A61B 17/32 |
| JP | 2013-031493 A | | 2/2013 | |
| JP | 2013-031544 A | | 2/2013 | |
| JP | 2013-085596 A | | 5/2013 | |

* cited by examiner

*Primary Examiner* — Steven M Cernoch
(74) *Attorney, Agent, or Firm* — Harness, Dickey & Pierce, P.L.C.

(57) ABSTRACT

A liquid ejection device includes: a nozzle including a nozzle opening through which a liquid is ejected; a liquid transfer tube through which the liquid is transferred to the nozzle; and a first tube with the nozzle and the liquid transfer tube being provided therein, having a first end and a second end, and having a first opening at the first end, in which the nozzle opening is positioned closer to a second end side than the first opening of the first tube, and when a position where the liquid ejected from the nozzle becomes a droplet is set as a droplet formation position, and a distance from the nozzle opening to the droplet formation position is set as a droplet formation distance, a distance between the nozzle opening and the first opening is equal to or greater than the droplet formation distance.

10 Claims, 8 Drawing Sheets

LIQUID EJECTION DEVICE

The present application is based on, and claims priority from JP Application Serial Number 2019-140788, filed Jul. 31, 2019, the disclosure of which is hereby incorporated by reference herein in its entirety.

BACKGROUND

1. Technical Field

The present disclosure relates to a liquid ejection device.

2. Related Art

There has been a liquid ejection device that performs operations such as cleaning, deburring, peeling, trimming, excising, incising, and crushing on an operation target by ejecting a pressurized liquid from a nozzle to collide with the operation target.

For example, JP-A-2013-31544 discloses a water jet knife having a micro pump, an outlet channel linking tube linked to the micro pump, and a link channel tube linked to the outlet channel linking tube, in which a living tissue of an affected area can be excised. A nozzle having an opening from which a fluid is ejected is press-fitted into a tip end of the link channel tube. The water jet knife includes a water amount adjustment unit provided around the tip end of the link channel tube. The water amount adjustment unit has a water supply tube, a suction tube, and an outer wall provided concentrically in this order from an inside so as to surround the link channel tube and the nozzle. The water supply tube is used to supply and store water into the outer wall. The suction tube is used to suction and discharge the water in the outer wall.

The link channel tube and the nozzle are independent of the water supply tube and the suction tube, and positions of the link channel tube and the nozzle can be adjusted in a vertical direction, that is, in a channel direction of water when the water is ejected from the nozzle.

According to the water jet knife disclosed in JP-A-2013-31544, as described above, the positions of the link channel tube and the nozzle are adjustable with respect to the water supply tube and the suction tube provided so as to surround the link channel tube and the nozzle. Therefore, it is also possible to retreat the link channel tube and the nozzle toward a base end side with respect to tip ends of the water supply tube and the suction tube positioned outside.

However, when the nozzle is retreated toward the base end side with respect to positions of the tip ends of the water supply tube and the suction tube on the outside, flying of water ejected from the nozzle may become unstable depending on a retreat amount. Specifically, when the water ejected from the nozzle hits the operation target, the water is scattered. Then, the scattered water may interfere with the flying of water that is newly ejected from the nozzle. When such a phenomenon is generated, since water newly ejected from the nozzle cannot fly stably, efficiency of various operations to be performed by causing water to collide with the operation target is reduced.

SUMMARY

A liquid ejection device according to an application example of the present disclosure includes: a nozzle including a nozzle opening through which a liquid is ejected; a liquid transfer tube through which the liquid is transferred to the nozzle; and a first tube with the nozzle and the liquid transfer tube being provided inside, having a first end and a second end, and having a first opening at the first end, in which the nozzle opening is positioned closer to the second end side than the first opening of the first tube, and when a position where the liquid ejected from the nozzle becomes a droplet is set as a droplet formation position, and a distance from the nozzle opening to the droplet formation position is set as a droplet formation distance, a distance between the nozzle opening and the first opening is equal to or greater than the droplet formation distance.

DESCRIPTION OF EXEMPLARY EMBODIMENTS

Hereinafter, preferred embodiments of a liquid ejection device of the present disclosure will be described in detail with reference to the accompanying drawings.

1. First Embodiment

First, a liquid ejection device according to a first embodiment will be described.

Figure 1:
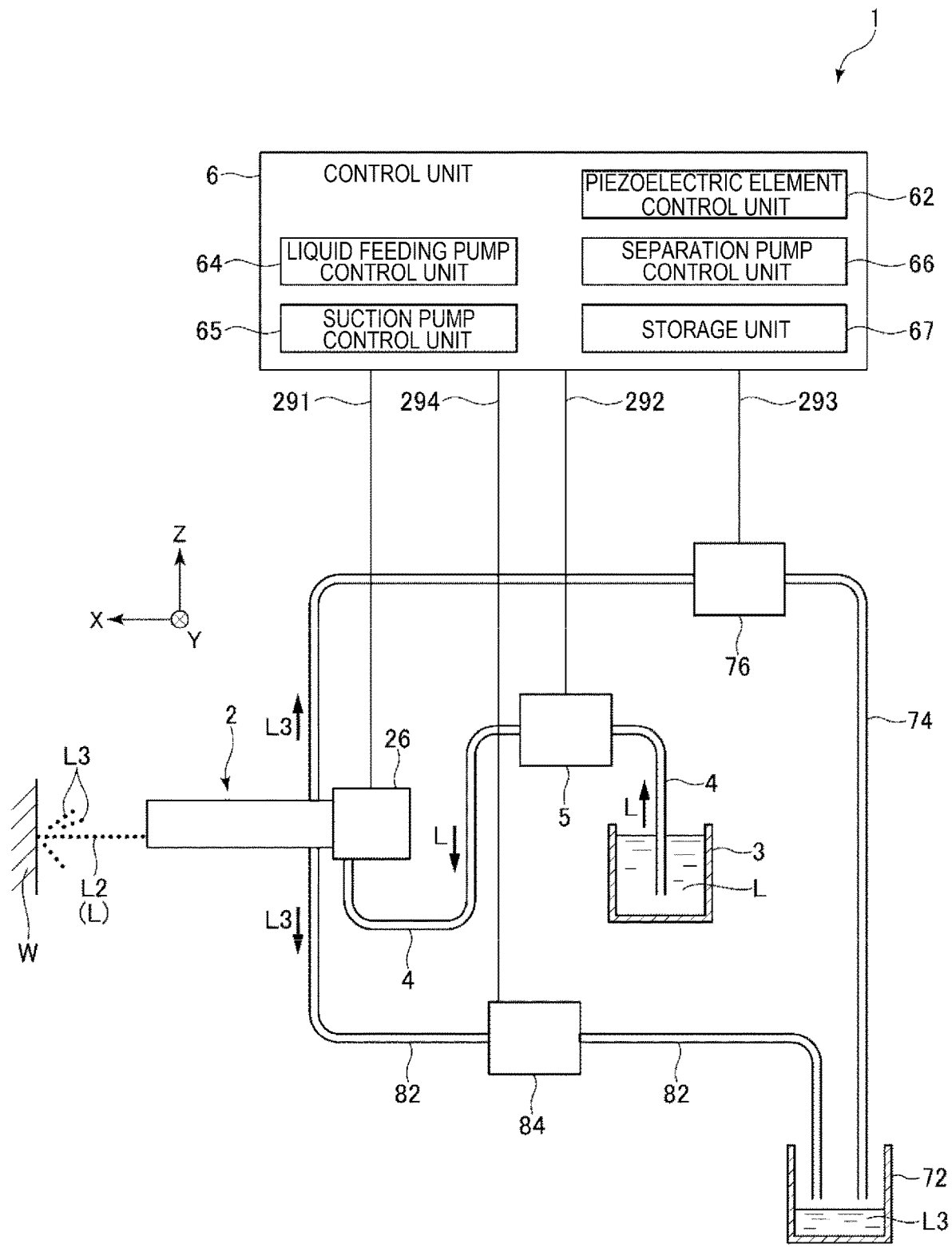
FIG. 1 is a schematic view showing a liquid ejection device according to a first embodiment.
Figure 2:
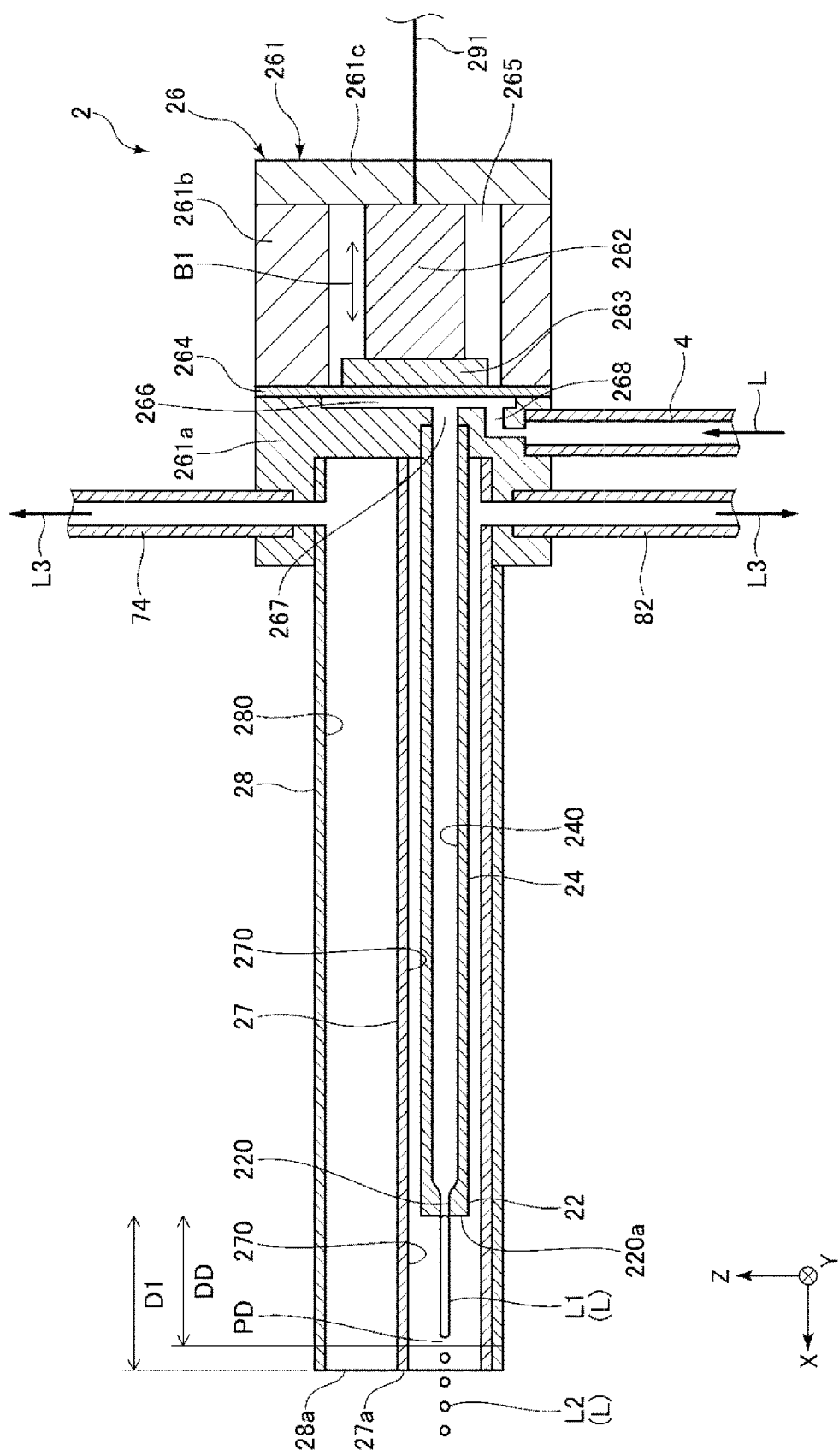
FIG. 2 is a cross-sectional view showing a nozzle unit of the liquid ejection device shown in FIG. 1.

FIG. 1 is a schematic view showing the liquid ejection device according to the first embodiment. FIG. 2 is a cross-sectional view showing a nozzle unit of the liquid ejection device shown in FIG. 1.

A liquid ejection device 1 shown in FIG. 1 includes a nozzle unit 2, a liquid container 3 that stores a liquid L, a liquid supplying tube 4 that links the nozzle unit 2 and the liquid container 3, a liquid feeding pump 5, and a control unit 6. Such a liquid ejection device 1 performs various operations by ejecting the liquid L from the nozzle unit 2 and causing the liquid L to collide with an operation target W. Examples of the various operations include cleaning, deburring, peeling, trimming, excising, incising, and crushing.

The liquid ejection device 1 shown in FIG. 1 includes a collection container 72 that stores a drainage liquid L3 suctioned by the nozzle unit 2, a drainage liquid collection tube 74 that links the nozzle unit 2 and the collection container 72, and a suction pump 76. The liquid L after an operation is collected as the drainage liquid L3, so that reduced workability, deteriorated visual field, and the like due to remaining of the drainage liquid L3 can be prevented.

Further, the liquid ejection device 1 shown in FIG. 1 includes a separation tube 82 that links the nozzle unit 2 and the collection container 72, and a separation pump 84. As will be described in detail later, in the present embodiment, by depressurizing a vicinity of the liquid L ejected from the nozzle unit 2, disturbance of flying of the liquid L can be suppressed, and the flying can be stabilized.

Hereinafter, each unit of the liquid ejection device 1 will be described in detail.

1.1 Nozzle Unit

As shown in FIG. 2, the nozzle unit 2 includes a nozzle 22, a liquid transfer tube 24, and a vibration generation unit 26. Among these parts, the nozzle 22 ejects the liquid L towards the operation target W shown in FIG. 1. The liquid transfer tube 24 is a channel that links the nozzle 22 and the vibration generation unit 26. The liquid transfer tube 24 transfers the liquid L from the vibration generation unit 26 to the nozzle 22. Further, the vibration generation unit 26 applies vibration as indicated by an arrow B1 to the liquid L supplied from the liquid container 3 via the liquid supplying tube 4. By applying the vibration to the liquid L in this manner, a pressure of the liquid L to be ejected from the nozzle 22 periodically varies. Accordingly, when the liquid L ejected from the nozzle 22 becomes a droplet L2, the droplet L2 having a larger diameter is formed. As a result, operation efficiency of an operation performed using an erosion action of the droplet L2 can be increased.

For the convenience of description, an axis linking the nozzle 22 and the operation target W is defined as an X axis, and an axis that is orthogonal to the X axis and is an axis of the liquid supplying tube 4 in a vicinity of a portion linked to the vibration generation unit 26 is defined as a Z axis in the drawings of the present application. An axis orthogonal to both the X axis and the Z axis is defined as a Y axis. In the X axis, a direction from the nozzle 22 towards the operation target W is defined as an X-axis positive side or a tip end side, and an opposite direction is defined as an X-axis negative side or a base end side. Further, in the Z axis, a direction from the liquid supplying tube 4 towards the liquid transfer tube 24 is defined as a Z-axis positive side, and an opposite direction is defined as a Z-axis negative side.

Hereinafter, each part of the nozzle unit 2 will be described in detail.

The nozzle 22 is attached to a tip end portion of the liquid transfer tube 24. The nozzle 22 is internally provided with a nozzle channel 220 through which the liquid L passes. An inner diameter of a tip end portion of the nozzle channel 220 is smaller than an inner diameter of a base end portion of the nozzle channel 220. The liquid L transferred towards the nozzle 22 in the liquid transfer tube 24 is formed into a fine flow via the nozzle channel 220 and is ejected. The nozzle 22 shown in FIG. 2 may be a member different from the liquid transfer tube 24, or may be integrally formed with the liquid transfer tube 24.

The liquid transfer tube 24 is a tube that links the nozzle 22 and the vibration generation unit 26, and includes a liquid channel 240 that transfers the liquid L in the liquid transfer tube 24. The above nozzle channel 220 communicates with the liquid supplying tube 4 via the liquid channel 240. The liquid transfer tube 24 may be a straight tube or a curved tube.

The nozzle 22 and the liquid transfer tube 24 only need to have such rigidity that the nozzle 22 and the liquid transfer tube 24 do not deform when the liquid L is ejected. Examples of a constituent material of the nozzle 22 include a metal material, a ceramic material, and a resin material. Examples of a constituent material of the liquid transfer tube 24 include a metal material and a resin material, and the metal material is particularly preferably used.

An inner diameter of the nozzle channel 220 is appropriately selected according to an operation content, a material of the operation target W and the like, and is preferably, for example, 0.05 mm or more and 1.0 mm or less, and more preferably 0.10 mm or more and 0.30 mm or less.

The vibration generation unit 26 includes a housing 261, a piezoelectric element 262 and a reinforcing plate 263 provided in the housing 261, and a diaphragm 264.

The housing 261 has a box shape, and includes each part of a first case 261a, a second case 261b, and a third case 261c. Each of the first case 261a and the second case 261b has a cylindrical shape including a through hole penetrating from a base end to a tip end. The diaphragm 264 is interposed between an opening of the first case 261a on a base end side and an opening of the second case 261b on a tip end side. The diaphragm 264 is, for example, a film-shaped member having elasticity or flexibility.

The third case 261c has a plate shape. The third case 261c is fixed to an opening of the first case 261a on the base end side. Space formed by the second case 261b, the third case 261c, and the diaphragm 264 is an accommodation chamber 265. The accommodation chamber 265 accommodates the piezoelectric element 262 and the reinforcing plate 263. A base end of the piezoelectric element 262 is linked to the third case 261c, and a tip end of the piezoelectric element 262 is linked to the diaphragm 264 via the reinforcing plate 263.

The through hole of the first case 261a penetrates from the base end to the tip end. Such a through hole includes an area on the base end side having a relatively large inner diameter and an area on the tip end side having a relatively small inner diameter. Among the areas, the liquid transfer tube 24 is inserted into the area having the small inner diameter from an opening on the tip end side. In the area where the inner diameter is large, the diaphragm 264 is covered from the base end side. Space formed by the area having a large inner diameter and the diaphragm 264 is a liquid chamber 266.

Further, space between the liquid chamber 266 and the liquid transfer tube 24 is an outlet channel 267. On the other hand, an inlet channel 268 which is different from the outlet channel 267 communicates with the liquid chamber 266. One end of the inlet channel 268 communicates with the liquid chamber 266, and the other end thereof is inserted with the liquid supplying tube 4 described above from the Z-axis negative side. Accordingly, an internal channel of the liquid supplying tube 4 communicates with the inlet channel 268, the liquid chamber 266, the outlet channel 267, the liquid channel 240, and the nozzle channel 220. As a result, the liquid L supplied to the inlet channel 268 via the liquid supplying tube 4 is sequentially ejected through the liquid chamber 266, the outlet channel 267, the liquid channel 240, and the nozzle channel 220.

A wiring 291 is drawn out from the piezoelectric element 262 via the housing 261. The piezoelectric element 262 is electrically linked to the control unit 6 via the wiring 291. The piezoelectric element 262 vibrates so as to expand or contract along the X axis based on an inverse piezoelectric effect by a drive signal supplied from the control unit 6. When the piezoelectric element 262 expands, the diaphragm 264 is pushed to the X-axis positive side. Therefore, a volume of the liquid chamber 266 is decreased, and a pressure in the liquid chamber 266 is raised. Then, the liquid L in the liquid chamber 266 is sent to the outlet channel 267, and the liquid L in the nozzle channel 220 is ejected. On the other hand, when the piezoelectric element 262 contracts, the diaphragm 264 is pulled toward the X-axis negative side. Therefore, the volume of the liquid chamber 266 is enlarged, and the pressure in the liquid chamber 266 is reduced. Then, the liquid L in the outlet channel 267 is sent into the liquid chamber 266.

A vibration pattern of the piezoelectric element 262 may be a periodic pattern or a non-periodic pattern as long as it is a vibration pattern that can displace the diaphragm 264 along the X axis. When the vibration pattern is a periodic pattern, a frequency of the variation pattern may be constant or may vary. The piezoelectric element 262 may be an element that expands, contracts and vibrates along the X axis, or may be an element that flexes and vibrates.

The piezoelectric element 262 includes, for example, a piezoelectric body and an electrode provided on the piezoelectric body. Examples of a constituent material of the piezoelectric body include piezoelectric ceramics such as lead zirconate titanate (PZT), barium titanate, lead titanate, potassium niobate, lithium niobate, lithium tantalate, sodium tungstate, zinc oxide, barium strontium titanate (BST), strontium bismuth tantalate (SBT), lead metaniobate, and lead scandium niobate.

Further, the piezoelectric element 262 can be replaced with any element or mechanical element that can displace the diaphragm 264. Examples of such an element or a mechanical element include a magnetostrictive element, an electromagnetic actuator, and a combination of a motor and a cam.

The housing 261 only needs to have such rigidity that the housing 261 does not deform when the pressure in the liquid chamber 266 is raised or reduced.

The vibration generation unit 26 shown in FIG. 2 is provided at a base end portion of the liquid transfer tube 24, but a position of the vibration generation unit 26 is not particularly limited. For example, the vibration generation unit 26 may be provided in a middle of the liquid transfer tube 24 or may be provided at the tip end of the liquid transfer tube 24.

A drive frequency of the piezoelectric element 262 is not particularly limited. A waveform of the drive signal input into the piezoelectric element 262 may be a periodic waveform such as a sine wave, a rectangular wave, or a sawtooth wave, or a non-periodic waveform.

The vibration generation unit 26 may be provided as needed, and may be omitted.

As shown in FIG. 2, the nozzle unit 2 includes a separation tube 27, which is a first tube, and a suction tube 28, which is a second tube.

The separation tube 27 includes a separation channel 270 configured to be depressurized inside. The separation channel 270 communicates with an internal channel of the separation tube 82 provided on abase end side of the separation channel 270. Then, in the present embodiment, the separation channel 270 is depressurized by the separation pump 84 via the separation tube 82.

The separation tube 27 is provided such that outer peripheral surfaces of the nozzle 22 and the liquid transfer tube 24 are surrounded. In other words, the nozzle 22 and the liquid transfer tube 24 are inserted into the separation channel 270 of the separation tube 27.

Here, a tip end of the nozzle channel 220 is a nozzle opening 220a, and a tip end of the separation tube 27 is a first opening 27a. The nozzle opening 220a is positioned closer to the base end side than the first opening 27a of the separation tube 27. In other words, the nozzle opening 220a is retreated to the X-axis negative side from the first opening 27a of the separation tube 27.

On the other hand, a position where the liquid L ejected from the nozzle 22 becomes the droplet L2 is referred to as a droplet formation position PD. A distance from the nozzle opening 220a to the droplet formation position PD is referred to as a droplet formation distance DD. At this time, a distance D1 between the nozzle opening 220a retreated as described above and the first opening 27a is equal to or greater than the droplet formation distance DD.

Since the distance D1 is optimized in this manner, the separation channel 270 being space which is covered with the separation tube 27 and which is depressurized than an atmospheric pressure, is present at the tip end side of the nozzle opening 220a with a length of the distance D1. Due to the presence of such a space, the liquid L ejected from the nozzle 22 is separated from the liquid drainage L3 such as a reflected liquid flow and a suction liquid flow, and is protected. As a result, the liquid L can be ejected stably, and reduction of the operation efficiency of the operation performed using the erosion action of the droplet L2 can be prevented.

The reflected liquid flow refers to a liquid flow or droplets generated by the ejected liquid L colliding with the operation target W and being reflected. The suction liquid flow refers to a liquid flow or droplets generated by pulling the reflected liquid flow or the like accompanied by the suction performed by the above suction tube 28.

The separation tube 27 only needs to have such rigidity that the separation tube 27 does not deform when the separation channel 270 is depressurized. Examples of a constituent material of the separation tube 27 include a metal material, a ceramic material, a glass material, and a resin material, and the metal material is particularly preferably used. The separation tube 27 may be a straight tube or a curved tube.

Outer diameters of the nozzle 22 and the liquid transfer tube 24 are appropriately set according to the operation content, the material of the operation target W, and the like, and is preferably, for example, 1.0 mm or more and 10 mm or less, and more preferably 2.0 mm or more and 6.0 mm or less.

In this case, an inner diameter of the separation channel 270 is preferably 1.1 times or more and 10 times or less of the outer diameters of the nozzle 22 and the liquid transfer tube 24, and more preferably 1.5 times or more and 5.0 times or less. Accordingly, an appropriate gap is generated between the nozzle 22 or the liquid transfer tube 24 and the separation tube 27. As a result, a depressurization speed can be ensured as necessary and sufficient. Therefore, even if the drainage liquid L3 enters the tip end side of the nozzle opening 220a, the drainage liquid L3 can be quickly drawn into the separation channel 270. As a result, clearance of a path through which the liquid L is ejected can be ensured, and the ejection of the liquid L can be more stabilized.

On the other hand, the inner diameter of the separation channel 270 of the separation tube 27, which is the first tube, is preferably 1.88 times or more of an inner diameter of the nozzle opening 220a, and more preferably 3.00 times or more. Accordingly, even if an ejected flow L1 ejected from the nozzle 22 is changed to the droplet L2 and a diameter is enlarged by combining droplets L2, a probability that the enlarged droplet L2 comes into contact with an inner surface of the separation channel 270 can be reduced. That is, it is known that a magnification when the droplets L2 are naturally assembled and increased in size is about 1.88 times on an average, so that by setting the inner diameter of the separation channel 270 to the value or more, the probability of the droplet L2 coming into contact with the inner surface of the separation channel 270 can be reduced.

Although the separation channel 270 according to the present embodiment is the space which is depressurized than the atmospheric pressure, a pressure of the separation channel 270 may be the atmospheric pressure, or may be higher than the atmospheric pressure as will be described later. Even in such a case, since the clearance of the path through which the liquid L is ejected can be ensured, the liquid L can be ejected stably. However, from a viewpoint of obtaining sufficient stability, the separation channel 270 is preferably depressurized or pressurized as described later, as in the present embodiment.

The suction tube 28 is positioned outside the separation tube 27. An outer peripheral surface of the separation tube 27 is surrounded by the suction tube 28. Accordingly, not only the separation tube 27 but also the nozzle 22 and the liquid transfer tube 24 inserted into the separation tube 27 are also inserted into a suction channel 280 of the suction tube 28.

As described above, the suction tube 28 is internally provided with the suction channel 280 configured to suction the liquid. The suction channel 280 communicates with an internal channel of the drainage liquid collection tube 74 provided on a base end side of the suction channel 280. Then, the suction channel 280 suctions the liquid by the suction pump 76 via the drainage liquid collection tube 74.

The suction tube 28 is provided in such a manner, so that the drainage liquid L3 such as the above reflected liquid flow and suction liquid flow can be prevented from remaining in a periphery of the operation target W. If the drainage liquid L3 remains, the newly flying droplet L2 collides with the drainage liquid L3. In this case, an impact pressure from the droplets L2 cannot be applied to the operation target W, and the operation efficiency is reduced. Therefore, the reduction of the operation efficiency can be prevented by suctioning the drainage liquid L3. In addition, the deteriorated visual field accompanied by the scattering of the drainage liquid L3 is prevented, so that the reduction of the operation efficiency can be prevented.

An inner diameter of the suction channel 280 is preferably 1.5 times or more and 10 times or less of an outer diameter of the separation tube 27, and more preferably 2.0 times or more and 8.0 times or less. Accordingly, an appropriate gap is generated between the separation tube 27 and the suction tube 28. As a result, even if the drainage liquid L3 contains residues or the like after the operation, sticking in the suction channel 280 can be prevented. The depressurization speed can be ensured as necessary and sufficient. Therefore, the drainage liquid L3 in the suction channel 280 can be quickly suctioned and the drainage liquid L3 can be more reliably prevented from remaining in the periphery of the operation target W.

The suction tube 28 only needs to have such rigidity that the suction tube 28 does not deform when the suction channel 280 is depressurized. Examples of a constituent material of the suction tube 28 include a metal material, a ceramic material, a glass material, or a resin material. The suction tube 28 may be a straight tube or a curved tube.

The suction tube 28 may be opaque, or may be translucent, or transparent. In the latter case, it becomes easy to visually recognize the separation tube 27 and the droplet L2 that jumps out of the separation tube 27 through the suction tube 28. As a result, positional accuracy of the operation can be increased.

Further, when the suction tube 28 is translucent or transparent, the separation tube 27 may also be translucent or transparent. Accordingly, since the nozzle 22 can be directly visually recognized, the positional accuracy of the operation can be further increased.

1.2 Liquid Container

The liquid container 3 stores the liquid L. The liquid L stored in the liquid container 3 is supplied to the nozzle unit 2 via the liquid supplying tube 4.

As the liquid L, for example, water is preferably used, but an organic solvent may be used. Any solute may be dissolved in the water or the organic solvent, and any dispersoid may be dispersed in the water or the organic solvent.

The liquid container 3 may be a sealed container or an open container.

1.3 Liquid Feeding Pump

The liquid feeding pump 5 is provided in the middle or an end portion of the liquid supplying tube 4. The liquid L stored in the liquid container 3 is suctioned by the liquid feeding pump 5 and supplied to the nozzle unit 2 at a predetermined pressure.

The control unit 6 which will be described later is electrically linked to the liquid feeding pump 5 via a wiring 292. The liquid feeding pump 5 has a function of changing a pressure of the liquid L to be supplied based on a drive signal output from the control unit 6.

1.4 Collection Container

The drainage liquid L3 suctioned by the suction tube 28 as described above is sent to the collection container 72 via the drainage liquid collection tube 74. The collection container 72 stores the drainage liquid L3.

In the present embodiment, the separation pump 84 is also a pump used to depressurize the separation channel 270. Therefore, when the drainage liquid L3 is drawn into the separation channel 270, the drainage liquid L3 is also sent to the collection container 72 via the separation tube 82. The drainage liquid L3 sent via the separation tube 82 may be stored in a container different from the collection container 72.

1.5 Suction Pump and Separation Pump

The suction pump 76 is provided in the middle or an end portion of the drainage liquid collection tube 74. The drainage liquid L3 can be suctioned and sent to the collection container 72 by depressurizing the suction channel 280 by the suction pump 76. On the other hand, the separation pump 84 is provided in the middle or an end portion of the separation tube 82. The drainage liquid L3 can be suctioned and sent to the collection container 72 by depressurizing the separation channel 270 by the separation pump 84.

Therefore, from a viewpoint of a function of depressurization, the suction pump 76 and the separation pump 84 are equivalent. The suction pump 76 suctions the drainage liquid L3 more strongly in the suction channel 280, and plays a role of facilitating direct collision of the droplet L2 with the operation target W, and preventing the deteriorated visual field accompanied by the scattering of the drainage liquid L3. On the other hand, the separation pump 84 plays a role of removing the scattered drainage liquid L3 when a part of a flow of the drainage liquid L3 suctioned toward a suction channel 280 side is scattered in the separation channel 270.

Therefore, it is preferable that an ultimate pressure accompanied by the depressurization by the suction pump 76 is lower than an ultimate pressure accompanied by the depressurization by the separation pump 84. Accordingly, most of the drainage liquid L3 is suctioned into the suction channel 280, and a probability that the drainage liquid L3 enters a separation channel 270 side can be reduced. In addition, even if a part of the scattered drainage liquid L3 enters the separation channel 270, an amount thereof can be decreased to a small amount. Accordingly, the flying of the liquid L ejected from the nozzle 22 can be prevented from being interfered by the drainage liquid L3, and the flying can be more stabilized.

The ultimate pressure accompanied by the depressurization by the suction pump 76 is preferably 90% or less, more preferably 1% or more and 80% or less of the ultimate pressure accompanied by the depressurization by the separation pump 84. Accordingly, the probability that the drainage liquid L3 enters the separation channel 270 side can be particularly reduced, and a flight path of the ejected flow L1 can be prevented from being bent as the separation channel 270 is depressurized more than necessary.

The above ultimate pressure refers to the lowest pressure measured on an intake side when each pump operates.

1.6 Control Unit

The control unit 6 is electrically linked to the nozzle unit 2 via the wiring 291. The control unit 6 is electrically linked to the liquid feeding pump 5, the suction pump 76, and the separation pump 84 via wirings 292, 293, and 294.

The control unit 6 shown in FIG. 1 includes a piezoelectric element control unit 62, a liquid feeding pump control unit 64, a suction pump control unit 65, a separation pump control unit 66, and a storage unit 67.

The piezoelectric element control unit 62 outputs a drive signal to the piezoelectric element 262. Driving of the piezoelectric element 262 is controlled by the drive signal. Accordingly, the diaphragm 264 can be displaced by, for example, a predetermined frequency and a predetermined displacement amount.

The liquid feeding pump control unit 64 outputs a drive signal to the liquid feeding pump 5. Driving of the liquid feeding pump 5 is controlled by the drive signal. Accordingly, the liquid L can be supplied to the nozzle unit 2 at, for example, a predetermined pressure and a predetermined drive time.

The suction pump control unit 65 outputs a drive signal to the suction pump 76. Driving of the suction pump 76 is controlled by the drive signal. Accordingly, the suction pump 76 can be driven at, for example, a predetermined pressure and a predetermined drive time, such that a suction speed and a suction time of the drainage liquid L3 suctioned by the suction tube 28 can be adjusted.

The separation pump control unit 66 outputs a drive signal to the separation pump 84. Driving of the separation pump 84 is controlled by the drive signal. Accordingly, the separation pump 84 can be driven at, for example, a predetermined pressure and a predetermined drive time, such that a suction speed and a suction time of the drainage liquid L3 suctioned by the separation tube 27 can be adjusted.

The control unit 6 can control two or more of the driving of the piezoelectric element 262, the driving of the liquid feeding pump 5, the driving of the suction pump 76, and the driving of the separation pump 84 in cooperation with each other.

Functions of the control unit 6 are implemented by hardware such as an arithmetic unit, a memory, and an external interface.

Examples of the arithmetic unit include a central processing unit (CPU), a digital signal processor (DSP), and an application specific integrated circuit (ASIC).

Examples of the memory include a read only memory (ROM), a flash ROM, a random access memory (RAM), and a hard disk.

1.7 Operation of Liquid Ejection Device

Next, an operation of the liquid ejection device 1 will be described.

The liquid L stored in the liquid container 3 is suctioned by the liquid feeding pump 5 and supplied to the vibration generation unit 26 at a predetermined pressure via the liquid supplying tube 4. In the vibration generation unit 26, the pressure of the liquid L supplied to the liquid chamber 266 is changed. The pressure change causes the liquid L to generate a pulsation flow. The pulsation flow refers to the flow of the liquid L whose flow rate or flow speed varies with time. A varying pattern may be a regular pattern or an irregular pattern. The liquid L accompanied by the pulsation flow is ejected through the liquid channel 240 and the nozzle channel 220 shown in FIG. 2.

Figure 3:
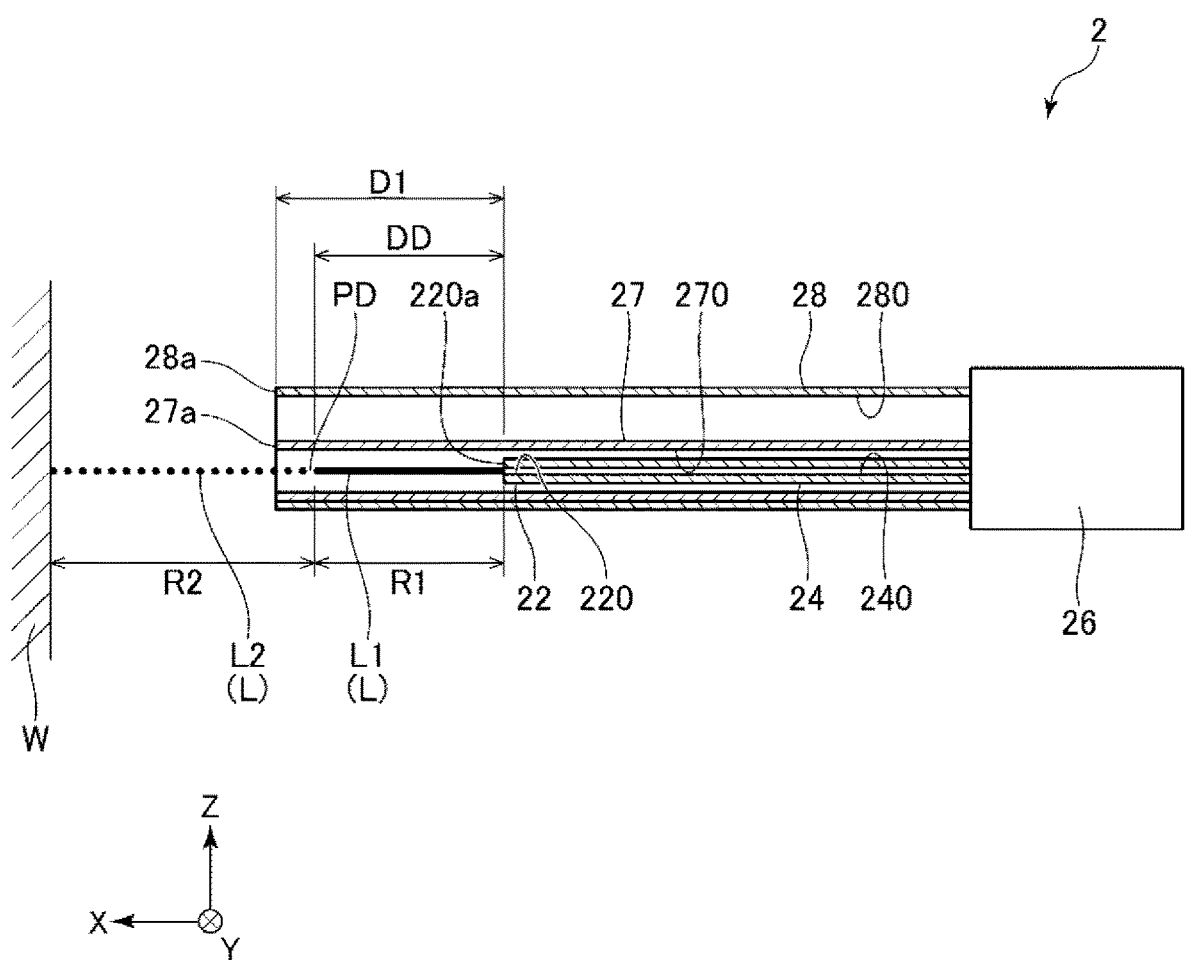
FIG. 3 is a cross-sectional view schematically showing a shape of a liquid ejected from the liquid ejection device.

The liquid L ejected from the liquid ejection device 1 as described above flies in the air while showing a behavior as shown in FIG. 3, for example. FIG. 3 is a cross-sectional view schematically showing a shape of the liquid L ejected from the liquid ejection device 1.

The liquid L ejected from the liquid ejection device 1 flies as the continuous columnar ejected flow L1 immediately after the ejection. Such a continuous ejected flow L1 is generated in an area within a predetermined distance from a tip end of the nozzle 22. This area is referred to as a "continuous flow area R1". On the other hand, a shape of the continuous ejected flow L1 is disturbed and the ejected flow L1 is changed to the droplets L2 on an operation target W side from the continuous flow area R1. An area where the droplets L2 are generated is referred to as a "droplet flow area R2". When such a droplet L2 collides with the operation target W, the impact pressure can be increased even at the same flow rate as compared with a case in which the ejected flow L1 collides with the operation target W. As a result, the operation efficiency can be increased.

Here, the above droplet formation distance DD is the distance from the nozzle opening 220a to the droplet formation position PD. As shown in FIG. 3, the droplet formation position PD refers to a position at which the columnar ejected flow L1 starts to change to the droplet L2.

Figure 4:
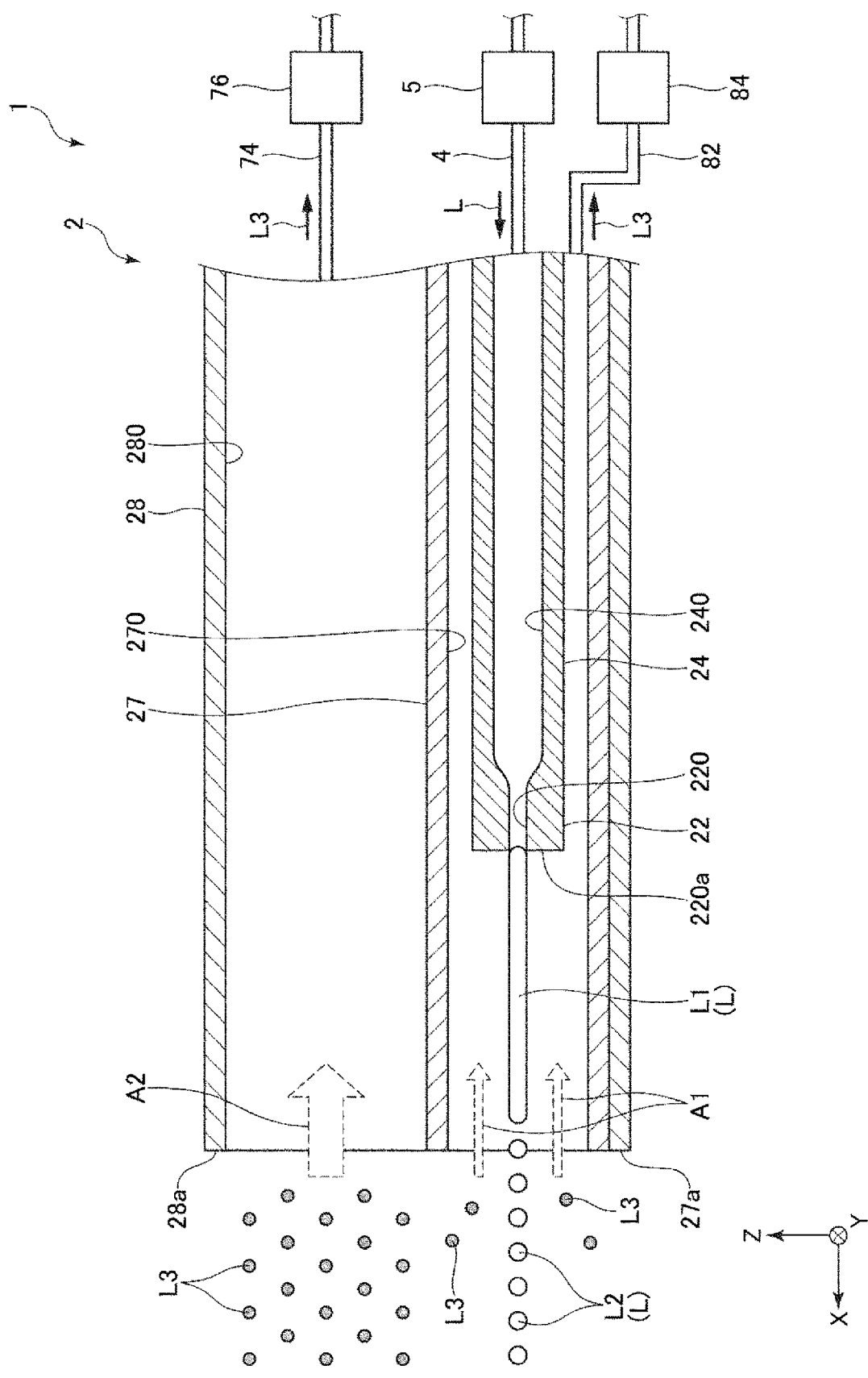
FIG. 4 is a diagram schematically showing a vicinity of a tip end portion of the nozzle unit shown in FIG. 3.
Figure 5:
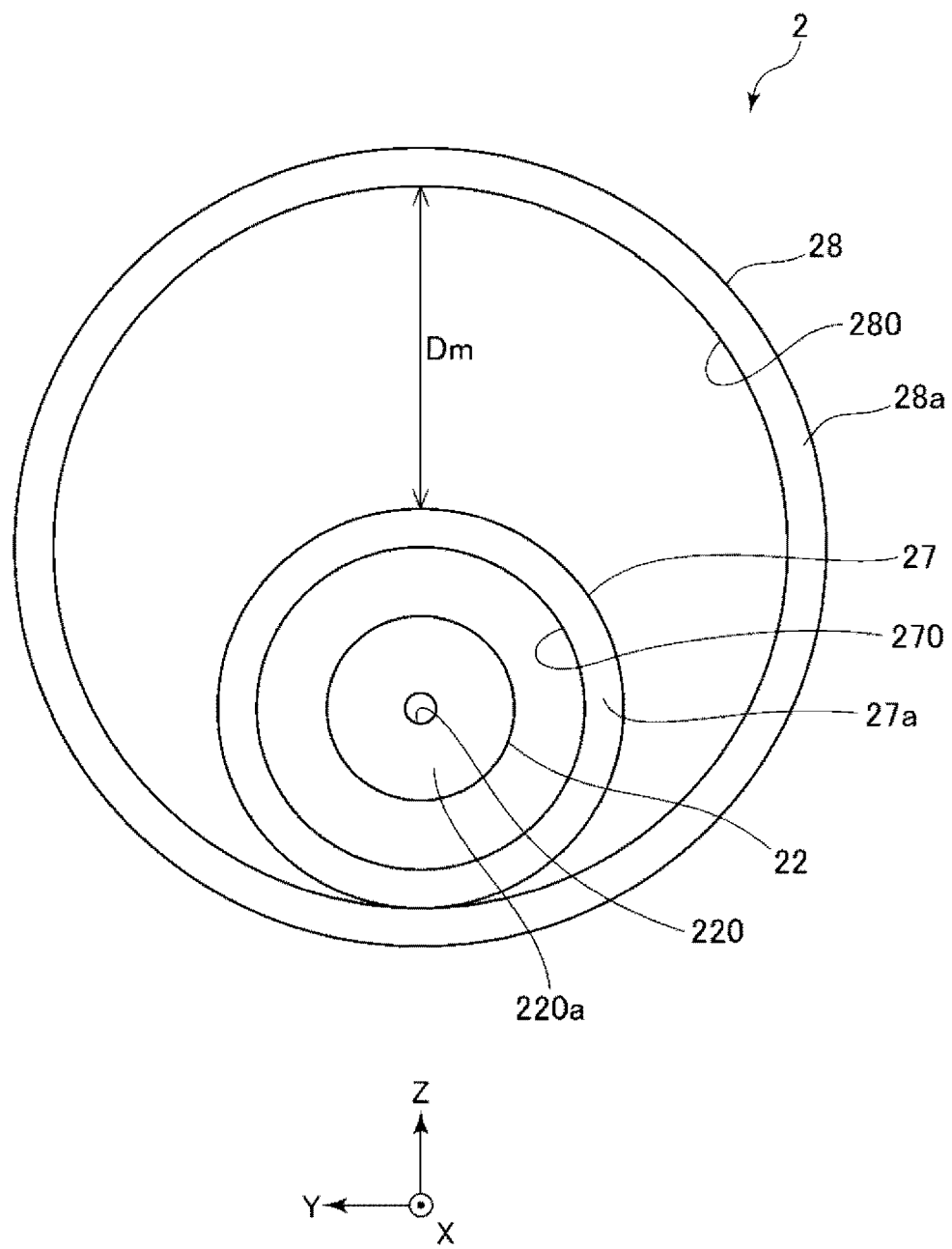
FIG. 5 is a diagram showing the nozzle unit shown in FIG. 4 as viewed from a tip end side.

FIG. 4 is a diagram schematically showing a vicinity of the tip end portion of the nozzle unit 2 shown in FIG. 3. FIG. 5 is a view showing the nozzle unit 2 shown in FIG. 4 as viewed from the tip end side.

In the present embodiment, as described above, the distance D1 between the nozzle opening 220a and the first opening 27a is equal to or greater than the droplet formation distance DD. Therefore, the liquid L ejected from the nozzle opening 220a flies as the continuous columnar ejected flow L1 while flying over the droplet formation distance DD. Then, when the ejected flow L1 reaches the droplet formation position PD, the droplet L2 is generated. Therefore, if the flying of the ejected flow L1 is interfered by some obstacle or the like, the generation of the droplet L2 is also inhibited, which leads to the reduction of the operation efficiency by the liquid ejection device 1.

In contrast, in the present embodiment, since the distance D1 is equal to or greater than the droplet formation distance DD, the ejected flow L1 can be caused to fly in the separation channel 270 inside the separation tube 27. Therefore, the ejected flow L1 can be protected by the separation tube 27, and the flying can be stabilized. As a result, the droplet L2 can be stably generated, and the operation efficiency with respect to the operation target W can be increased.

In addition, an indication of the droplet formation position PD can be obtained by visually checking the position of the first opening 27a of the separation tube 27. That is, since the droplet formation position PD is positioned in the separation channel 270, it is ensured that the droplet flow area R2 is positioned on the tip end side from the first opening 27a. Then, an operator can efficiently perform an operation that makes full use of a benefit of the impact pressure by the droplet L2 without being conscious of the droplet formation position PD.

Even when the drainage liquid L3 enters the separation channel 270, the drainage liquid L3 can be suctioned and removed by the separation pump 84 as indicated by an arrow A1 in FIG. 4. As a result, the flying of the ejected flow L1 can be stabilized, and the droplet L2 can be stably generated.

The distance D1 may be equal to or greater than the droplet formation distance DD, and is preferably 1.01 times or more and 2.00 times or less of the droplet formation distance DD, and more preferably 1.10 times or more and 1.50 times or less of the droplet formation distance DD. When the distance D1 is within this range, the flying of the ejected flow L1 can be more stabilized. If the distance D1 exceeds the above upper limit value, the distance D1 is too long compared with the droplet formation distance DD, so that the flight path of the droplet L2 may be disturbed, a flying speed may be reduced, and the erosion action on the operation target W may be reduced.

A position of the first opening 27a and a position of the nozzle opening 220a are preferably relatively movable. Accordingly, since the distance D1 can be varied according to the droplet formation distance DD, the above magnification can be appropriately selected.

As shown in FIG. 5, the nozzle 22 is preferably disposed concentrically with the separation tube 27. Accordingly, a periphery of the ejected flow L1 ejected from the nozzle 22 can be uniformly depressurized. As a result, the flying of the ejected flow L1 can be more stabilized, and thereafter the droplet L2 can be more reliably generated. It is not essential that the nozzle 22 is disposed concentrically with the separation tube 27, and both axes thereof may be shifted.

On the other hand, the drainage liquid L3 generated by the droplets L2 colliding with the operation target W and being reflected is suctioned by the suction tube 28. Here, a tip end of the suction tube 28 is referred to as a second opening 28a. When an inside of the suction channel 280 is depressurized by the suction pump 76, as indicated by an arrow A2 in FIG. 4, the drainage liquid L3 remaining in a vicinity of the second opening 28a can be suctioned and removed. Accordingly, the drainage liquid L3 can be prevented from remaining in the periphery of the operation target W, and the newly flying droplet L2 can be prevented from colliding with the drainage liquid L3. As a result, the impact pressure of the droplet L2 can be sufficiently applied to the operation target W, and the reduction of the operation efficiency can be prevented.

In FIG. 4, the position of the first opening 27a along the X axis and a position of the second opening 28a along the X axis coincide with each other, but these positions may be shifted from each other.

For example, when the position of the first opening 27a is shifted to the X-axis positive side compared with the position of the second opening 28a, the drainage liquid L3 and the ejected flow L1 are more easily distinguished in space. In addition, since the separation tube 27 at a position close to the ejected flow L1 can be directly visually checked, the operator can easily grasp a position of the ejected flow L1. On the other hand, since the separation tube 27 can be prevented from coming into contact with the operation target W when the position of the first opening 27a is shifted to the X-axis negative side with respect to the position of the second opening 28a, damage to the separation tube 27 can be prevented.

As described above, the liquid ejection device 1 according to the present embodiment includes the nozzle 22 including the nozzle opening 220a that ejects the liquid L, the liquid transfer tube 24 that transfers the liquid L to the nozzle 22, and the separation tube 27, which is the first tube, having the nozzle 22 and the liquid transfer tube 24 provided therein, having a tip end (first end) and a base end (second end), and having the first opening 27a at the tip end. The nozzle opening 220a is positioned closer to the base end side than the first opening 27a of the separation tube 27. Then, when the position where the liquid L ejected from the nozzle 22 becomes the droplet L2 is set as the droplet formation position PD, and the distance from the nozzle opening 220a to the droplet formation position PD is set as the droplet formation distance DD, the distance D1 between the nozzle opening 220a and the first opening 27a is equal to or greater than the droplet formation distance DD.

According to such a liquid ejection device 1, since the clearance of the path through which the liquid L is ejected can be ensured, the liquid L can be ejected stably. As a result, the droplet L2 can be stably generated, and various operations can be performed by the droplet L2 colliding with the operation target W.

In the liquid ejection device 1 according to the present embodiment, as described above, a pressure inside the separation tube 27, which is the first tube, is lower than the atmospheric pressure. Accordingly, even when the drainage liquid L3 enters the tip end side of the nozzle opening 220a, the drainage liquid L3 can be quickly drawn into the separation channel 270. As a result, the clearance of the path through which the liquid L is ejected can be ensured, and the ejection of the liquid L can be more stabilized.

The liquid ejection device 1 further includes the suction tube 28 as the second tube in which the separation tube 27 as the first tube is provided. Then, a pressure of the suction channel 280 inside the suction tube 28 is preferably set to be lower than the atmospheric pressure and lower than the pressure of the separation channel 270 inside the separation tube 27. Accordingly, most of the drainage liquid L3 is suctioned into the suction channel 280, and the probability that the drainage liquid L3 enters the separation channel 270 side can be reduced. In addition, even if a part of the scattered drainage liquid L3 enters the separation channel 270, the amount thereof can be decreased to a small amount. Accordingly, the flying of the liquid L ejected from the nozzle 22 can be prevented from being interfered by the drainage liquid L3, and the flying can be more stabilized.

In FIG. 5, the separation tube 27 is disposed non-concentrically with the suction tube 28. Specifically, an outer surface of the separation tube 27, which is the first tube, is fixed to an inner surface of the suction channel 280 of the suction tube 28, which is the second tube. Then, the separation tube 27 is disposed so as to be eccentric with respect to the suction tube 28. Accordingly, the path through which the ejected flow L1 flies and a path through which the suctioned drainage liquid L3 passes can be easily distinguished in space. As a result, the probability of the drainage liquid L3 interfering with the flying of the ejected flow L1 can be further reduced. Further, according to such a non-concentric arrangement, a maximum distance Dm between the outer surface of the separation tube 27 and the inner surface of the suction channel 280 can be ensured longer than that when the separation tube 27 is disposed concentrically with the suction tube 28. As a result, even when a foreign matter is mixed in the drainage liquid L3, the foreign matter is less likely to be stuck in the suction channel 280.

2. Second Embodiment

Next, a liquid ejection device according to the second embodiment will be described.

Figure 6:
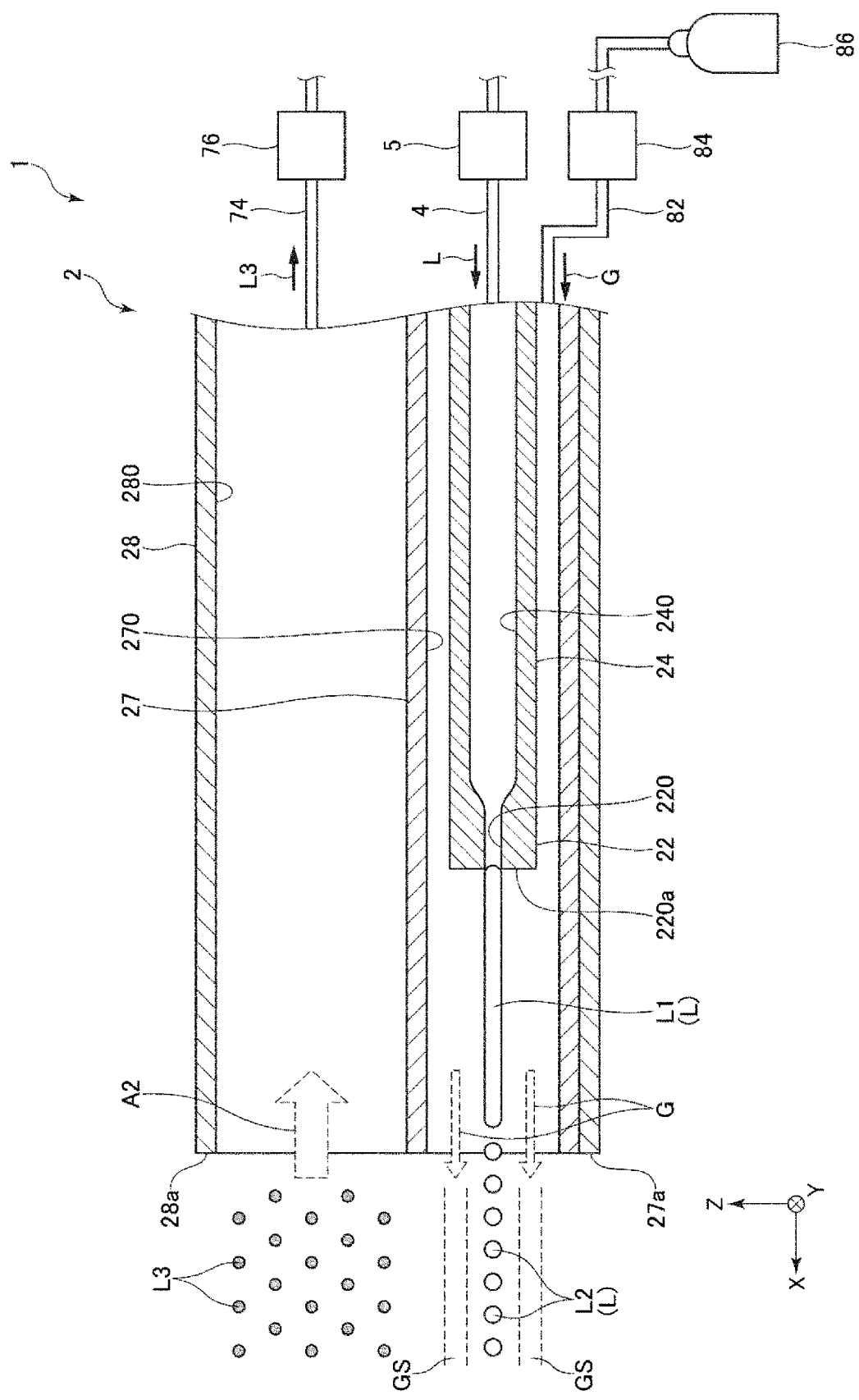
FIG. 6 is a cross-sectional view showing a liquid ejection device according to a second embodiment.

FIG. 6 is a cross-sectional view showing the liquid ejection device according to the second embodiment.

Hereinafter, the second embodiment will be described, and differences from the first embodiment will be mainly described in the following description, and description of similar matters is omitted. In FIG. 6, similar components as those in the first embodiment are denoted by the same reference numerals.

The second embodiment is similar to the first embodiment except that a configuration of the separation pump 84 is different.

In the first embodiment described above, the separation pump 84 has a function of depressurizing the separation channel 270. In contrast, in the present embodiment, the separation pump 84 has a function of pressurizing the separation channel 270.

That is, in the liquid ejection device 1 according to the present embodiment, the pressure inside the separation tube 27, which is the first tube, is higher than the atmospheric pressure. Accordingly, it is possible to release gas G from the separation channel 270 to the outside. As a result, it is possible to form a shield GS with the gas G along the path along which the liquid L ejected from the nozzle 22 flies. The shield GS prevents the drainage liquid L3 from entering the tip end side of the nozzle opening 220a. As a result, the clearance of the path through which the liquid L is ejected can be ensured, and the ejection of the liquid L can be more stabilized. The shield GS also contributes to increasing positional accuracy of the flight path of the droplet L2 and preventing a reduction in the flying speed even after the liquid L changes to the droplet L2. As a result, the operation efficiency can be particularly increased.

In the present embodiment, a gas storage unit 86 that stores the gas G to be supplied to the separation channel 270 is included. The gas G stored in the gas storage unit 86 is supplied to the separation channel 270 by the separation pump 84.

In this case, a maximum pressure of the separation channel 270 may be higher than the atmospheric pressure, and is preferably 1.1 atm or more and 10 atm or less, more preferably 1.2 atm or more and 5.0 atm or less. By setting the pressure of the separation channel 270 within the above range, the drainage liquid L3 can be sufficiently prevented from entering the tip end side of the nozzle opening 220a, and an adverse effect on the ejection of the liquid L can be prevented by the shield formed of the gas.

Any gas may be used for the gas G, and examples of the gas include air, nitrogen gas, and argon gas.

Also in the second embodiment as described above, the similar effect as that of the first embodiment can be obtained.

3. Third Embodiment

Next, a liquid ejection device according to a third embodiment will be described.

Figure 7:
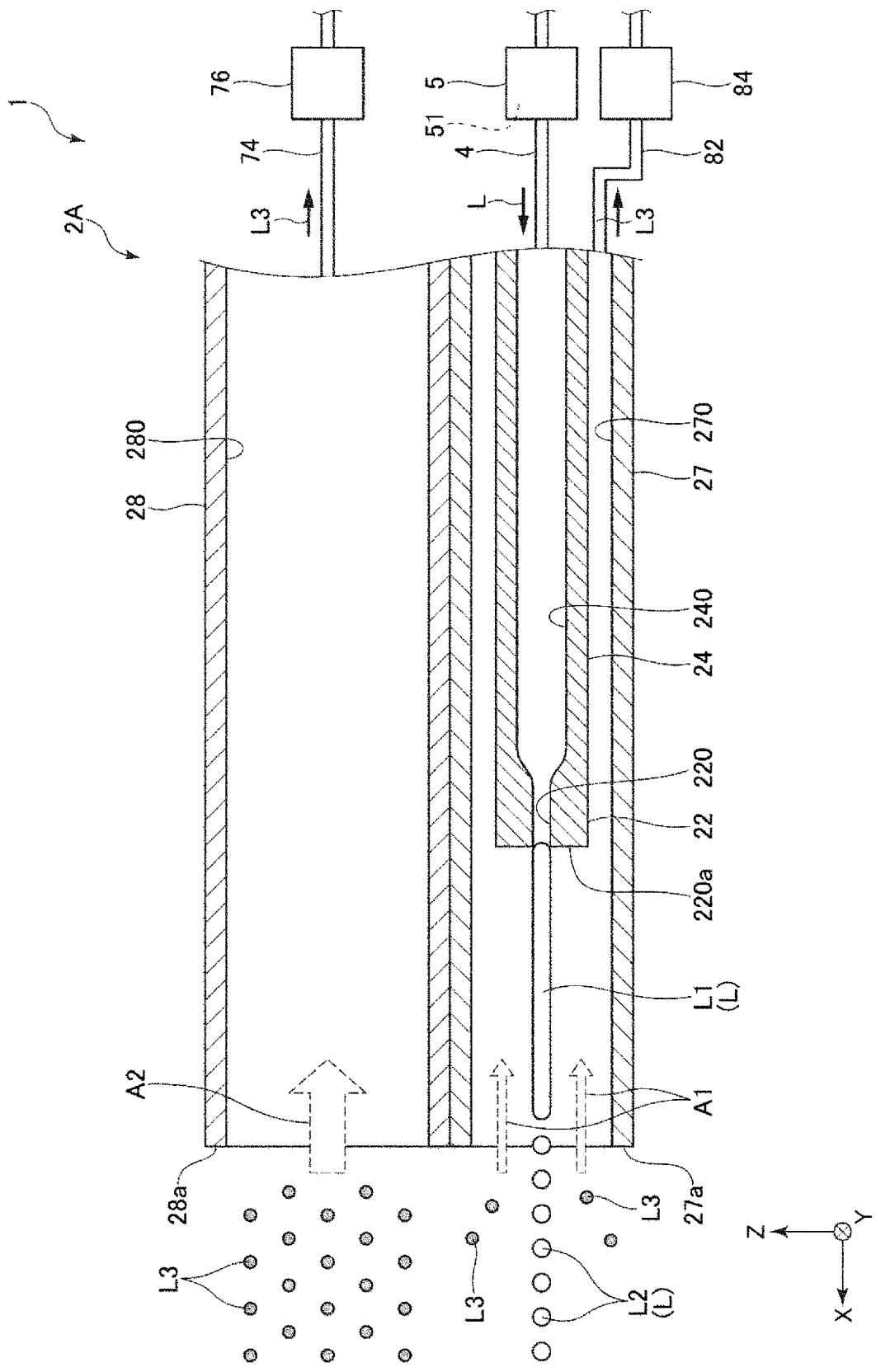
FIG. 7 is a cross-sectional view showing a liquid ejection device according to a third embodiment.
Figure 8:
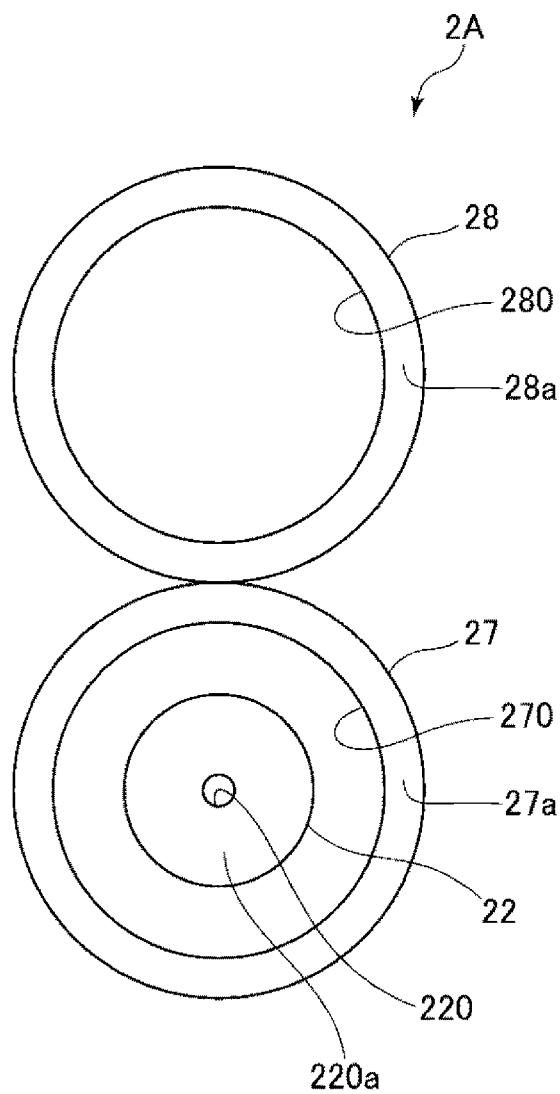
FIG. 8 is a diagram showing a nozzle unit shown in FIG. 7 as viewed from a tip end side.

FIG. 7 is a cross-sectional view showing the liquid ejection device according to the third embodiment. FIG. 8 is a view showing a nozzle unit 2A shown in FIG. 7 as viewed from the tip end side.

Hereinafter, the third embodiment will be described, and differences from the first embodiment will be mainly described in the following description, and description of similar matters is omitted. In FIG. 6, similar components as those in the first embodiment are denoted by the same reference numerals.

The third embodiment is similar to the first embodiment except that a configuration of the nozzle unit 2 is different.

In the nozzle unit 2 according to the first embodiment described above, the separation tube 27 is inserted into the suction channel 280 inside the suction tube 28. In contrast, in a nozzle unit 2A according to the present embodiment, the separation tube 27 is provided outside the suction channel 280.

That is, as shown in FIGS. 7 and 8, the liquid ejection device 1 according to the present embodiment further includes the suction tube 28 that is the second tube provided together with the separation tube 27 that is the first tube. Then, similar to the first embodiment, the pressure of the suction channel 280 inside the suction tube 28 is preferably set to be lower than the atmospheric pressure and lower than the pressure of the separation channel 270 inside the separation tube 27. Accordingly, most of the drainage liquid L3 is suctioned into the suction channel 280, and the probability that the drainage liquid L3 enters the separation channel 270 side can be reduced. In addition, even if a part of the scattered drainage liquid L3 enters the separation channel 270, the amount thereof can be decreased to a small amount. Accordingly, the flying of the liquid L ejected from the nozzle 22 can be prevented from being interfered by the drainage liquid L3, and the flying can be more stabilized.

Further, in the present embodiment, as shown in FIG. 8, a distance between a position of the nozzle 22 and a position of the suction channel 280 can be set larger than that in the first embodiment. Accordingly, the path through which the ejected flow L1 flies and a path through which the suctioned drainage liquid L3 passes can be easily distinguished in space. As a result, the probability of the drainage liquid L3 interfering with the flying of the ejected flow L1 can be further reduced.

The liquid feeding pump 5 according to the present embodiment includes a built-in check valve 51. By providing such a check valve 51, it is possible to prevent the liquid L from flowing back through the liquid supplying tube 4 accompanied by the vibration applied to the liquid L in the vibration generation unit 26 shown in FIG. 2. The check valve 51 may be provided independently in the middle of the liquid supplying tube 4. The first embodiment and the second embodiment may include the check valve 51 similarly.

In FIG. 7, an axis of the separation tube 27 and an axis of the suction tube 28 are substantially parallel, but a positional relationship thereof is not particularly limited, and may be non-parallel.

In FIG. 7, the position of the first opening 27a along the X axis and the position of the second opening 28a along the X axis coincide with each other, but these positions may be shifted from each other.

Further, although the separation tube 27 and the suction tube 28 are in contact with each other in FIGS. 7 and 8, they may be separated from each other.

The pressure of the separation channel 270 may be higher than atmospheric pressure.

Also in the third embodiment as described above, similar effects as those of the first and second embodiments can be obtained.

Although the liquid ejection device according to the present disclosure is described above based on the illustrated embodiments, the present disclosure is not limited to the embodiments.

For example, in the liquid ejection device according to the present disclosure, a configuration of each unit in the embodiments may be replaced with any configuration having similar function, and any configuration may be added to the configuration in the embodiments.

The arrangement of the vibration generation unit is not limited to the positions in the embodiments described above, and may be any position as long as it is a position at which vibration can be applied to the liquid transferred through liquid transfer tube. Further, the liquid ejection device of the present disclosure may include a plurality of vibration generation units. In this case, two or more of the above embodiments may be used in combination.

Further, although the vibration generation unit according to the embodiments adopts a method of vibrating the diaphragm, a method of vibrating the liquid transfer tube may be adopted.

What is claimed is:

1. A liquid ejection device comprising:
a liquid transfer tube extending along a first direction, a liquid being transferred through the liquid transfer tube, the liquid transfer tube having a first end and a second end outwardly opposite to each other, the first end having a nozzle, the nozzle including a nozzle opening through which the liquid is ejected as a continuous ejected flow, the second end having a liquid inlet to which the liquid is supplied, the liquid flowing in a liquid flow direction in the liquid transfer tube;
a liquid feeding pump configured to feed the liquid to the liquid inlet of the liquid transfer tube from a liquid container;
a piezoelectric device configured to apply vibration along the first direction to the liquid in the liquid transfer tube via another structure;
a first tube extending along the first direction, the liquid transfer tube being located inside of the first tube, the first tube having a third end and a fourth end, the third end of the first tube further outwardly extending from the first end of the liquid transfer tube along the first direction by a first distance;
a separation tube connected to the first tube at an area directly adjacent to the fourth end of the first tube;
a separation pump connected to the separation tube to suck air in an inside of the first tube via the separation tube, the air in the first tube flowing in an air flow direction; and
a second tube extending along the first direction, the first tube being located inside of the second tube, the second tube having a fifth end and a sixth end, the fifth and sixth ends being located adjacent to the third and fourth ends, respectively,
wherein a position where the continuous ejected flow of the liquid from the nozzle opening splits so as to generate a droplet is set as a droplet formation position, and a distance along the first direction from the nozzle opening to the droplet formation position is set as a second distance,
the first distance is more than the second distance, and the second distance is more than a half of the first distance,
the liquid flow direction is opposite to the air flow direction,
the piezoelectric device is spaced apart from the liquid,
the first tube is disposed non-concentrically with the second tube
an inner diameter of the first tube is in a range of 1.5 times to 5.0 times of an outer diameter of the liquid transfer tube, and
an inner diameter of the second tube is in a range of 2.0 times to 8.0 times of an outer diameter of the first tube.

2. The liquid ejection device according to claim 1, wherein
a pressure inside the second tube is lower than atmospheric pressure and lower than a pressure inside the first tube.

3. The liquid ejection device according to claim 2, wherein
an outer surface of the first tube is fixed to an inner surface of the second tube.

4. The liquid ejection device according to claim 1, wherein
an outer surface of the first tube is fixed to an inner surface of the second tube.

5. The liquid ejection device according to claim 1, wherein
the inner diameter of the first tube is 1.88 times or more of an inner diameter of the nozzle opening.

6. The liquid ejection device according to claim 1, wherein
a pressure inside the first tube is lower than or higher than atmospheric pressure.

7. The liquid ejection device according to claim 2, wherein
the pressure inside the first tube is lower than or higher than atmospheric pressure.

8. The liquid ejection device according to claim 3, wherein
a pressure inside the first tube is lower than or higher than atmospheric pressure.

9. The liquid ejection device according to claim 4, wherein
a pressure inside the first tube is lower than or higher than atmospheric pressure.

10. The liquid ejection device according to claim 5, wherein
a pressure inside the first tube is lower than or higher than atmospheric pressure.

* * * * *